United States Patent [19]

White

[11] 3,960,499

[45] June 1, 1976

[54] BIOLOGICAL TEST APPARATUS

[75] Inventor: Fred K. White, Glen Ellyn, Ill.

[73] Assignee: Miles Laboratories, Inc., Elkhart, Ind.

[22] Filed: Feb. 18, 1975

[21] Appl. No.: 550,603

[52] U.S. Cl............................ 23/253 R; 204/180 G; 204/169; 204/299; 427/37
[51] Int. Cl.² .......................................... B01R 5/00
[58] Field of Search.......... 204/180 R, 180 G, 180 S, 204/299; 23/253 R; 210/31 C, 198 C

[56] References Cited
UNITED STATES PATENTS

| | | | |
|---|---|---|---|
| 3,635,808 | 1/1972 | Elevitch | 204/180 G |
| 3,691,054 | 9/1972 | Cawley | 204/299 |
| 3,766,047 | 10/1973 | Elevitch | 204/299 |
| 3,875,044 | 4/1975 | Renn et al. | 204/299 |

Primary Examiner—John H. Mack
Assistant Examiner—A. C. Prescott
Attorney, Agent, or Firm—Louis E. Davidson

[57] ABSTRACT

An improved biological test apparatus has an organoplastic support surface which has been treated to become hydrophilic, said surface supporting an aqueous gel employed for the desired test mechanism. The hydrophilic treatment enables the aqueous gel to be in uniform close adherent contact with the support surface. This prevents the formation of an uneven gel thickness and improves the adherence of the gel to the support surface during storage and subsequent use.

8 Claims, No Drawings

BIOLOGICAL TEST APPARATUS

BACKGROUND AND PRIOR ART

Numerous tests on biological materials are carried out in an aqueous gel medium. Illustrative test procedures are immunodiffusion, electrophoresis, immunoelectrophoresis and immunological reactions. In such procedures, the aqueous gel, such as agarose, may contain reactants. In general, such test procedures are carried out with aqueous gels contained within glass containers or supported by glass surfaces. Such glass material is not completely satisfactory, since it is quite fragile, resulting in damage to the test apparatus during shipment, storage and/or use.

Efforts have been made in the prior art to replace glass with organoplastic materials, since such organoplastic materials are generally less expensive than glass and are considerably less fragile. Such replacement with organoplastic materials has not been completely satisfactory, because the aqueous gel-forming suspensions and resulting gels do not adhere well to prior art organoplastic support surfaces. This poor adhesion can cause undesirable air bubbles to be formed at the gel-support surface interface when the gel-forming aqueous suspension is spread onto such surface, and the suspension may not flow uniformly over the support surface producing a gel layer having uneven thickness or rippled portions which interfere with subsequent use of the apparatus. In some immunodiffusion reactions test wells are dug out of the gel layer. When there is reduced adherence between the gel layer and the support surface, the entire gel layer can undesirably be lifted away from the support surface during the formation of these test wells. During storage of the test apparatus, the gel layer can tend to become at least partially dehydrated. This dehydration causes a slight shrinking of the gel layer and can cause a prior art organoplastic apparatus to have undesirable separation of the gel layer from the organoplastic support surface.

There is thus a commercial need for biological test apparatus having a uniform close adherent contact between an aqueous gel and an organoplastic support surface.

SUMMARY OF THE INVENTION

In accordance with the present invention a biological test apparatus is provided comprising an organoplastic support surface which has been treated to become hydrophilic and an aqueous gel in uniform close adherent contact with said hydrophilic surface.

DESCRIPTION OF THE INVENTION

The organoplastic support surface can be formed by molding suitable organoplastic materials, such as polystyrene, polypropylene, styrene-acrylonitrile copolymers, polycarbonate, cellulose acetate propionate, cellulose acetate butyrate, nitrile-acrylonitrile-styrene copolymers, polyacrylate, polymethacrylate, acrylonitrile-butadiene-styrene coplymers and the like. The suitable organoplastic materials preferably contain a reactive carbon-carbon double bond. This support surface can be formed as a surface member alone or it can be an integral part of an organoplastic container into which the aqueous gel and the subsequent test specimens and reactants are introduced.

The surface of the organoplastic support member can be rendered hydrophilic in any suitable well-known manner. It is known, for example, that treatment of polystyrene surfaces with concentrated sulfuric acid will provide the introduction of sulfate radicals to the polystyrene surface. This renders the surface hydrophilic. It is believed that the sulfate is being introduced at the vinyl carbon-carbon double bond position in the styrene polymer molecules. The application of an electrical discharge to a suitable organoplastic surface, such as polystyrene, in the presence of oxygen will produce a surface layer of styrene oxide. This likewise renders the surface hydrophilic. The oxygen is introduced at the carbon-carbon double bond position in the polystyrene molecules to form an oxirane structure.

Suitable gels for use in the apparatus of the present invention are aqueous gels of agarose, algin, carrageen, polysaccharides, carboxymethyl cellulose, carboxyethyl cellulose, starch-polyacrylonitrile graft copolymers and the like. The invention will be further described in the following Example.

EXAMPLE

An immunodiffusion test apparatus was produced in the following manner. A shallow polystyrene tray was molded in a conventional manner. The upper surface of the bottom of the tray was then exposed to an electrical discharge of about 500,000 volts and a few microamperes in the presence of air for about 5 seconds. The discharge took place between two electrodes located in close proximity to the polystyrene surface. This resulted in a stable hydrophilic coating of styrene oxide being formed on the tray surface. An aqueous suspension of agarose containing about one weight percent agarose was poured into the tray. The aqueous suspension easily flowed over and covered the tray bottom to form a uniform layer without requiring the use of a spatula, for example, to spread the suspension. The suspension then solidified as a gel. The resulting gel layer formed a uniform close adherent contact with the hydrophilic surface. There were no undesirable ripples or bubbles in the gel layer. The gel layer remained in satisfactory adherent contact with the support surface even upon extended storage. The resulting biological test apparatus can be used in the same manner as similar prior art apparatus, and it represents a significant advance in the art because of the improved adhesion between the gel layer and the hydrophilic organoplastic supporting surface.

What is claimed is:

1. Biological test apparatus comprising an organoplastic support surface which has been treated to become hydrophilic and an aqueous gel in uniform close adherent contact with said hydrophilic surface.

2. Apparatus according to claim 1 wherein the hydrophilic organoplastic surface is an integral part of an organoplastic container.

3. Apparatus according to claim 1 wherein the aqueous gel is an agarose gel.

4. Apparatus according to claim 1 wherein the organoplastic support surface is formed from material selected from the class consisting essentially of polystyrene, polypropylene, styrene-acrylonitrile copolymers, polycarbonate, cellulose acetate propionate, cellulose acetate butyrate, nitrile-acrylonitrile-styrene copolymers, polyacrylate, polymethacrylate, and acrylonitrile-butadiene-styrene copolymers.

5. Apparatus according to claim 1 wherein the hydrophilic surface is obtained by electric discharge treatment of the organoplastic material.

6. Apparatus according to claim 1 wherein the hydrophilic surface is obtained by sulfuric acid treatment of the organoplastic material.

7. Apparatus according to claim 1 wherein sulfate radicals are introduced to the surface of the organoplastic material to render it hydrophilic.

8. Apparatus according to claim 1 wherein oxygen atoms are introduced at the carbon-carbon double bond positions of the organoplastic surface molecules to form an oxirane structure which renders the surface hydrophilic.

* * * * *